(12) United States Patent
Taoufik

(10) Patent No.: US 9,885,714 B2
(45) Date of Patent: Feb. 6, 2018

(54) IMMUNOLOGICAL METHOD FOR DETECTING ACTIVE JCV INFECTION

(75) Inventor: Yassine Taoufik, Paris (FR)

(73) Assignees: Assistance Publlque—Hopitaux de Paris, Paris (FR); Universite Paris—Sud 11, Orsay (FR)

( * ) Notice: Subject to any disclaimer, the term of this patent is extended or adjusted under 35 U.S.C. 154(b) by 0 days.

(21) Appl. No.: 13/254,503

(22) PCT Filed: Mar. 3, 2010

(86) PCT No.: PCT/EP2010/052670
§ 371 (c)(1),
(2), (4) Date: Dec. 14, 2011

(87) PCT Pub. No.: WO2010/100182
PCT Pub. Date: Sep. 10, 2010

(65) Prior Publication Data
US 2012/0094273 A1    Apr. 19, 2012

(30) Foreign Application Priority Data
Mar. 3, 2009   (EP) .................................... 09154228

(51) Int. Cl.
| | | |
|---|---|---|
| A61K 31/704 | (2006.01) | |
| C07J 1/00 | (2006.01) | |
| A61K 31/569 | (2006.01) | |
| A61K 31/58 | (2006.01) | |
| A61K 31/695 | (2006.01) | |
| G01N 33/569 | (2006.01) | |
| C12Q 1/70 | (2006.01) | |
| G01N 33/68 | (2006.01) | |

(52) U.S. Cl.
CPC ....... *G01N 33/56983* (2013.01); *C12Q 1/701* (2013.01); *G01N 33/56972* (2013.01); *G01N 33/6863* (2013.01); *G01N 2333/025* (2013.01); *G01N 2800/28* (2013.01); *G01N 2800/50* (2013.01)

(58) Field of Classification Search
CPC .............. C07K 16/081; C07K 2317/33; G01N 2333/025; G01N 2800/28; A61K 31/343; A61K 31/57; A61K 47/34
USPC .......................................................... 435/5
See application file for complete search history.

(56) References Cited

U.S. PATENT DOCUMENTS 7,662,912 B2 *  2/2010  Lacey ................... C12Q 1/708
                                                        530/300

FOREIGN PATENT DOCUMENTS

| WO | WO2006026746 | * | 9/2006 |
| WO | WO2007056463 | * | 5/2007 |
| WO | WO2007103112 | * | 9/2007 |

OTHER PUBLICATIONS

Petrovsky et al., Cytokine-based human whole blood assay for the detection of antigen-reactive T cells, 1995, Journal of Immunological Methods, 186:37-46.*
Lenz et al., Papillomavirus-like particles induce acute activatio of dendritic cells, 2001, Journal of Immunology, 166:5346-5355.*
Gasnault et al., Critical role of JC virus-specific CD4 T-cell responses in preventing progressive multifocal leukoencephalopathy, 2003, AIDS, 17:1443-1449.*
Koralnik et al., JC virus-specific cytotoxic T lymphocytes in Individuals with Progressive Multifocal Leukoencephalopathy, 2001, Journal of Virology, 75(7):3483-3487.*
BD Biosciences, Cytokine Detection in Antigen-Activated CD8 and CD4 T cells, 2002, FastImmune Cytokine System, 23-5195-02:pp. 1-16.*
Khalili et al., Neurology, 2007, 68(13):985-990.*
Gasnault, J., et al., "Analysis of anti-JCvirus CD4 T-Cell Response in Healthy Subjects and in HIV+ Patients with or without Progressive Multifocal Leukoencephalopathy," 9th Conf Retrovir Oppor Infect, Seattle, Wash. Feb. 24-28, 2002; 9: abstract No. 727-W.
Gasnault, J., et al., "Critical role of JC virus-specific CD4 T-cell responses ikn preventing progressive multifocal leukoencephalopathy," AIDS (2003), vol. 17, No. 10, pp. 1443-1449.
Khalili, K., et al., "Reactivation of JC virus and development of PML in patients with multiple sclerosis," Neurology (Mar. 27, 2007), vol. 68, pp. 985-990.
Petrovsky, N., et al., "Cytokine-based human whole blood assay for the detection of antigen-reactive T cells," Journal of Immunological Methods (1995), vol. 186, pp. 37-46.
Weber, F., et al., "Cellular and Humoral Immune Response in Progressive Multifocal Leukoencephalopathy," Annals of Neurology (May 2001), pp. 636-642.
Chen, Y. et al., "Asymptomatic reactivation of JC virus in patients treated with natalizumab." *N Engl J Med*, vol. 361(11), pp. 1067-1074, Sep. 10, 2009.
Hendel-Chavez, H. et al., "Immunological Hallmarks of JC Virus Replication in Multiple Sclerosis Patients on Long-Term Natalizumab Therapy." *Journal of Virology*, vol. 87(10), pp. 6055-6059, May 2013.
Jameson, S.C. et al., "Diversity in T cell memory: An embarrassment of riches." *Immunity*, vol. 31(6), pp. 859-871, Dec. 18, 2009 (author manuscript).
Jilek, S. et al., "Immune responses to JC virus in patients with multiple sclerosis treated with natalizumab: a cross-sectional and longitudinal study." *Lancet Neurol*, vol. 9, pp. 264-272, Jan. 29, 2010.
Kivisäkk, P. et al., "Natalizumab treatment is associated with peripheral sequestration of proinflammatory T cells." *Neurology*, vol. 72, pp. 1922-1930, Jun. 2, 2009.
Lanzavecchia, A. et al., "Understanding the generation and function of memory T cell subsets." *Current Opinion in Immunology*, vol. 17, pp. 326-332, Apr. 20, 2005.
Mancuso, R. et al., "JC virus detection and JC virus-specific immunity in natalizumab-treated Multiple Sclerosis patients." *Journal of Translational Medicine*, vol. 10, pp. 248-257, 2012.

(Continued)

*Primary Examiner* — Barry A Chestnut
(74) *Attorney, Agent, or Firm* — Polsinelli PC

(57) ABSTRACT

The invention relates to an immunological method for detecting an extra renal active infection by JC virus in a patient candidate for a treatment with an immunosuppressive treatment or during the course of this treatment.

14 Claims, No Drawings

(56) References Cited

OTHER PUBLICATIONS

Mazopust, D. et al., "Hidden memories: Front line memory T cells and early pathogen interception." *J Immunol.* vol. 188(12), pp. 5811-5817, Jun. 15, 2012 (author manuscript).
Obar, J.J. et al., "Memory CD8+ T cell differentiation." *Am N Y Acad Sci.*, vol. 251-266, Jan. 2010 (author manuscript).
Ojdana, D. et al., "Effector and memory CD4+ and CD8+ T cells in the chronic infection process." *Folia Histochemica et Cytobiologica*, vol. 46(4), pp. 413-417, 2008.
Sallusto, F. et al., "Central Memory and Effector Memory T Cell Subsets: Function, Generation and Maintenance." *Annu. Rev. Immunol.* vol. 22, pp. 745-763, 2004.
Van Leeuwen, E.M.M. et al., "Generation and Maintenance of Memory CD4+ T Cells." *Curr Opin Immunol.*, vol. 21(2), pp. 167-172, Apr. 2009 (author manuscript).
Yamane, H. et al., "Memory CD4+ T Cells: Fate Determination, Positive Feedback and Plasticity." *Cell Mol Life Sci.*, vol. 69(10), pp. 1577-1583, May 2012 (author manuscript).

\* cited by examiner

IMMUNOLOGICAL METHOD FOR DETECTING ACTIVE JCV INFECTION

RELATED APPLICATIONS

This application is a national stage application (under 35 U.S.C. § 371) of PCT/EP2010/052670, filed Mar. 3, 2010, which claims priority of European application 09154228.2 filed on Mar. 3, 2009.

The invention relates to an immunological method for detecting an extra renal active infection by JC virus in a patient candidate for a treatment with an immunosuppressive treatment or during the course of this treatment.

The increasing use of monoclonal antibodies (MAb) used for therapeutic immuno-modulation in autoimmune diseases is associated with an increased risk of opportunistic infections, some of them may be life threatening.

This is particularly true of the Progressive Multi-focal Leukoencephalopathy (PML), whose causative agent, the polyomavirus JC (or JCV) is able, under certain conditions of local or systemic immunosuppression, to actively infect and destroy oligodendrocytes and astrocytes, leading to multifocal areas of demyelination and severe associated neurologic dysfunction.

PML cases have been reported during the course of treatment of Lupus with Rituximab or Psoriasis with Efalizumab but particularly following treatment of Multiple Sclerosis (MS) and Crohn's disease treated with natalizumab, a monoclonal antibody directed against α4 β1-integrin (VLA-4).

The major side effect observed during treatment with natalizumab is the occurrence of PML, which has been observed with an estimated incidence of 1 to 1000 (Kappos L et al. 2007 Lancet Neurol. 6:431-41).

Occurrence of PML has also been observed in patients treated with Efalizumab for more than 3 years, and has led to the suspension of the marketing authorization of this MAb in Europe.

A period of prolonged exposure to MAbs, a previous exposure to immunosuppressive therapy, an immune deficiency (such as a CD4 T cell depletion) are probably contributing factors, but these factors are not necessarily present. Other risk factors exist, such as genetic factors related to the host or the level of pre-existing infection with JC virus.

It is therefore important to be able to identify subjects in whom exposure to MAb is associated with an increased risk to develop PML. This would improve the safety of such MAb. It is also important to monitor patients treated with MAb to determine any active infection by the JC virus in the central nervous system at an early stage, to be able to stop the MAb treatment before PML onset and irreversible neurological lesions.

Unfortunately, there is little to expect from markers such as JC virus DNA in urine detected by PCR) or the presence of JC virus antibodies in serum.

Indeed, JC virus infects a majority of the adult population with an active replication in renal epithelial cells associated with urinary excretion in a substantial proportion of infected individuals. Active replication of JC virus seems tolerated in the kidney, for reasons that remain to be determined (and do not necessarily lead to generation of detectable effector T-cells response), but not in extra-renal tissues and in particular in the CNS. Out of kidney, detection of this virus is rare in immunocompetent patients. In particular, detection of the virus in the cerebrospinal fluid has a very high specificity as regards PML diagnosis.

In a series of healthy adults with JC virus, no CD8 T effector response against the JC virus was detected in the blood. However, this type of response was detected in 67% in a cohort of HIV-infected patients with PML. In case of severe immuno-depression, the risk of a significant viral replication in the CNS may increase subsequently to the decrease of the immune pressure on pre-existing viruses in the CNS or to the invasion of CNS from peripheral reservoirs.

Gasnault et al. (AIDS 17, 2003, 1443-49) describe a test of T cell proliferation after activation of the Peripheral Blood Mononuclear Cells (PBMC) with purified JCV for 7 days. This test makes it possible to detect central memory CD4 T cells, which secrete IL-2, and give help to CD8 T cells, following antigen reactivation. This test is of particular interest in HIV patients, as these patients present a depletion of CD4 central memory T cells and loss of CD4 T cell proliferative responses against recall antigens such as tuberculin, cytomegalovirus, candidin (from *Candida albicans*) and the like. This test detects central memory cells including quiescent cells, the presence of which points at a contact with JCV. This can represent an old infection, a recent infection or an ongoing infection. In this article, detection of JC virus in urine is used as a marker of susceptibility to infection, in the absence of readily usable serologic tests.

Khalili et al (Neurology 68, 2007, 985-90) describes the state of the art relative to JCV and the development of PML. The authors describe in particular the relationships between JCV and the immune system. This document indicates that a cellular immune response, in particular from cytotoxic T lymphocytes is important to control the virus. In the paragraph related to JCV detection methods, the authors only cite detection of the viral load by PCR in the patient sample.

Weber et al (Ann Neurol 49, 2001, 636-42) studied the humoral and cellular response to PML in HIV negative or positive patients which have PML or not. Proliferation of PBMC and their ability to produce gamma-interferon and IL-10 has been studied after stimulation with JCV virus like particles, which express the VP1 protein. The authors clearly indicate that there is no correlation between PBMC proliferation or cytokines production and the presence of JCV DNA in PBMC (page 640 right column). Furthermore, PBMC proliferation is less in PML patients than in non-infected patients. Proliferation of the PBMC is observed after priming with the antigen for 4 days (page 638, left column), so that Weber et al investigate CD4 central memory T cells.

Petrovsky and Harrison (J Immunol Methods. 186, 1995, 37-46) describe an assay for detecting activated T cells in blood, by measurement of cytokines in whole blood.

Natalizumab, via its attachment to VLA-4, blocks the traffic of activated T lymphocytes (whether they are autoreactive or directed against infectious agents)) from the periphery to the central nervous system. However, the effect of this antibody on the peripheral activation of these cells, via dendritic cells presenting antigens from the CNS, and circulating from brain parenchyma to cervical lymph nodes, is not clearly determined and it is postulated that JC viral activity in the CNS can be indirectly identified at the periphery via the detection of JC virus specific effector T cell responses.

The invention thus relates to a method of detecting extra renal infection by JC virus, particularly in the central nervous system of a patient candidate for an immunosuppressive treatment, comprising the step of:

a) screening for the presence of activated T lymphocytes (effectors) against JC virus in a blood sample of said patient.

Indeed, the presence of such activated T lymphocytes shall indicate infection by JC virus in the central nervous system.

In the context of the present invention, an immunosuppressive treatment consists in the administration of a substance that will reduce the number, activity or traffic of cells of the immune system.

In particular, an immunosuppressive treatment according to the invention is of particular interest for patients having an auto-immune disease, such as psoriasis, lupus, Rheumatoid arthritis, Crohn disease or multiple sclerosis.

Such substances usable in an immunosuppressive treatment include:

Cytostatic agents (such as nitrogen mustards (cyclophosphamide), nitrosoureas, platinum compounds, folic acid analogues, such as methotrexate, purine analogues such as azathioprine and mercaptopurine, pyrimidine analogues, protein synthesis inhibitors, or cytotoxic antibiotics such as dactinomycin, anthracyclines, mitomycin C, bleomycin, or mithramycin), which inhibit cell division and are thus usually used for treating cancer, and may be used in an immunosuppressive treatment (in smaller doses than in the treatment of malignant diseases) to inhibit proliferation of T and/or B cells.

Drugs acting on immunophilins such as ciclosporin, tacrolimus, sirolimus which can also be used in an immunosuppressive treatment.

Antibodies which are sometimes used as a quick and potent immunosuppressive therapy to prevent the acute rejection reactions as well as a targeted treatment of lyphoproliferative or autoimmune disorders (e.g., anti-CD20 monoclonals).

In a preferred embodiment, said substance is a monoclonal antibody. Particular antibodies are directed against CD11 (such as Efalizumab sold as Raptiva™ by Genentech and Merck Serono), CD20 (such as Rituximab, sold as Rituxan™ and MabThera™ by Biogen Idec, Serono and Roche).

A particular monoclonal antibody usable to induce an immunosuppressive treatment according to the invention is natalizumab (sold as Tysabri™ by Biogen Idec and Elan) which is directed against the cellular adhesion molecule α4-integrin (α4 β1-integrin, VLA-4).

It is to be noted that said substance may be administered by itself, or together with another substance that will also modulate the immune response, such as another MAb, or a cytokine, such as Interferon β-1a or an immunosuppressive drug.

In a preferred embodiment, said screening is performed by detection of production of at least one inflammatory cytokine by said T lymphocytes upon presentation of epitopes of JC virus to said lymphocytes.

In an alternative embodiment, said screening is performed by detecting an increase of the mRNA for at least one inflammatory cytokine in said activated lymphocytes (as compared to non-activated lymphocytes). This can be performed by Reverse Transcription and Polymerase Chain Reaction (RT-PCR).

The sequences of various cytokines are known in the art and kits for detecting cytokines are commercially available. Assays for isolating mRNA and performing RT-PCR are also available. Quantitative RT-PCR Procedures have been described in Taoufik y et al., Blood 1997 89:2842-8: Taoufik Y et al., Eur cyto netw 1998 9:197-204; Durali D et al., Blood. 2003 102:4084-9. Cytokine mRNAs level (such as IFN-γ, IL-10, IL-4, TGF-β1) may be determined by real-time PCR technique with the TaqMan or light cycler chemistry as described in the above references.

The present method makes it possible to identify an effector T-lymphocyte immune response against the JC virus, in the periphery, that is linked to the presence of an out-of-kidney JC virus activity (and in particular of a JC virus activity in the CNS).

The detection of the activated T-lymphocytes is performed after a short exposure (within about 24 hours) to the epitopes of the virus.

Exposure time should go up to 48 hours, but a shorter exposure will better reflect the presence of activated T-lymphocytes in the harvested blood sample. Exposure time will thus preferably be between 12 and 36 hours, more preferably between 14 to 24 hours, most preferably between about 16 to 20 hours.

The method aims at the detection of in vivo activated effector T-cells (helper T-cells) that are present in the blood sample. The Presence of such cells supposes the existence of an active JC virus infection. Incubation of the patient sample with the virus epitopes shall thus not be too long, as a long-time incubation (a few days or weeks) could lead to detection of resting memory T-cells, the presence of which would not reflect an active infection.

This test (detection of cytokines after a short activation with purified JC virus) thus makes it possible to detect effector cells, secreting said cytokines, but having reduced ability to proliferate, and help CD8 T-lymphocytes, by contrast with the central memory cells. These cells have been activated in vivo by the antigen, and are thus re-stimulated in vitro for a short period of time. Presence of these effector cells reflects the presence of an active systemic infection.

In a preferred embodiment, said epitopes are presented to said lymphocytes by exposing said lymphocytes to purified JC virus. Use of a whole virus (rather than individual epitopes or antigens) makes it possible to take all viral epitopes into account. In particular, the use of purified JCV also allows activation of CD4 T cells through presentation of all potential MHC class II restricted virus epitopes by monocytes following internalization of whole viral particles.

When individual epitopes or antigens, or whole virus is used, viral peptide epitopes are preferably presented to the T lymphocytes by Antigen-Presenting Cells (APC), such as monocytes:macrophages or dendritic cells. These epitopes/antigens could be directly added in a whole blood sample or first incubated with said APC prior to co-incubation of the APC and the T-lymphocytes.

In a preferred embodiment, said cytokine is a cytokine linked with Th-1-type immunological responses.

The cytokine is thus preferably comprised in the group consisting of gamma-interferon (IFN-γ), and interleukin 2 (IL-2) and the like.

Production of the cytokine by the activated T-lymphocytes is detected by any method known in the art. In particular, it is possible to detect the presence of the cytokine in the supernatant by ELISA (Enzyme-Linked ImmunoSorbent Assay), flow cytometry related method (such as a LUMINEX assay developed by Luminex, Austin, Tex., USA), by ELISPOT (Enzyme-linked immunosorbent spot) procedure or intracellularly by flow cytometry. Kits for ELISA detection are available in the art, and can be obtained, in particular for IFN-γ, from Thermo Scientific, Rockford, Ill., USA (Thermo Scientific Pierce Human Interferon gamma (IFN gamma) ELISA Kit), or from Abcam, Cambridge, Mass., USA (Human Interferon gamma ELISA Kit—2×96 Well Plates (ab46045)). Kits for detecting production or intra cellular expression of IFN-γ, and various interleukins can also be obtained from other suppliers (such as MabTech, R&D Systems, Becton Dickinson, Milteny Biotechs, Coulter Immunotech . . . ).

Presence of positive (with PHA, phytohaemagglutanin) and negative (without virus) controls makes it possible to determine the actual increase in production of the cytokine upon presence of the virus and allows the control of the validity of the procedure.

In a first embodiment, said screening is performed on said blood sample. In another embodiment, said screening is performed on the nuclear cells present in the blood sample. In another embodiment, said screening is performed on isolated peripheral blood monocytes cells (PBMC), or on isolated T lymphocytes from said blood sample.

PBMC may be isolated by methods known in the art, such as the CPT (cell preparation tubes) or the ficoll separation. Usable methods are described in Nilsson et al. (Clin Vaccine Immunol. 2008 April; 15(4): 585-589).

CD4+ and CD8+ cells may be isolated from whole peripheral blood by immunomagnetic bead separation (Dynabeads, Dynal Biotech, Oslo, Norway).

The method of the invention may also comprise the step of b) harvesting said blood sample from said patient prior to step a).

The method of the invention may be completed when it further comprises the step of screening or quantifying for the presence of JC virus in a cerebrospinal fluid sample from said patient. This would confirm the first diagnosis obtained by presence of activated T-lymphocytes against JC virus in the periphery.

Looking for JC viral DNA in cerebrospinal fluid on may be performed by a polymerase-chain-reaction (PCR) or quantitative PCR assay. It is to be noted that, although this method is known in the art, it is not applicable on a large scale and on a routine basis, as it is very invasive for the patient (need to harvest cerebrospinal fluid). This second step b) is thus preferably used only on patients presenting activated T-lymphocytes.

Methods for detecting JC virus in cerebrospinal fluid are described in Weber et al. (1994, Aids 8, 49-57), Fong et al. (1995, J. Clin. Microbiol., 33, 484-486), McGuire et al. (1995, Ann. Neurol. 37, 395-399; published erratum appears in Ann. Neurol. (1995) 37, 687)).

A Method for quantifying JCV DNA is described in Taoufik et al., J Inf Dis (1998). 178, 1816. or in Taoufik Y et al., AIDS (2000) 14:758-9

The method of the invention may be performed on patients who had not yet received an immunosuppressive treatment, in order to determine whether they are at risk of developing PML upon treatment.

It may also be performed on patients who are already receiving an immunosuppressive treatment, in order to determine whether they actually present extra renal active JC virus infection in particular in the CNS. In case presence of activated T-lymphocytes is detected (indicating presence of JC virus infection), the immunosuppressive treatment would be withheld or interrupted.

If no activated T-lymphocytes are detected, infection is not present, and the immunosuppressive treatment can thus be started or continued.

Regularly repeating the method of the invention makes it possible to monitor the risk of infection with JC virus during the course of an immunosuppressive treatment, and in particular natalizumab treatment.

It is also of interest on patients who present a sign or symptom of Progressive Multi-focal Leukoencephalopathy.

The method of the invention may also be performed prior and/or further to having evaluated the patient by a magnetic resonance imaging (MRI) scan.

The invention also relates to the use of JCV epitopes (whole purified virus or individual epitopes or antigens) as priming epitopes, in order to detect activated effector T cells in a blood sample of a patient, wherein said patient is candidate for an immunosuppressive treatment.

The invention also relates to a kit containing JCV epitopes and means for measuring a Th1-type cytokine, such as interferon-gamma or interleukin-2. As mentioned above, one can use whole purified virus or individual epitopes or antigens.

EXAMPLE

Technical Procedure

Purified JC virus is used: MAD-4 strain, ATCC VR-1583 purified by differential centrifugation and sold by LGC standard, Molsheim, France) titrated at $10^{5.75}$ corresponding to a $TCID_{50}/0.2$ ml in 7 days on COS-7 cells (ATCC CRL—1651).

10 µl of this preparation is used for presentation to 200 000 PBMC.

5 ml of blood is harvested from a patient and mixed with EDTA for preventing clotting. This sample is divided in aliquots of 1 ml each.

50 µl of purified virus is added to a first aliquot.

1 µg of PHA is added to the second aliquot to make a positive control, whereas a third aliquot corresponds to the negative control.

Incubation is performed at 37° C. for 18 hours and the samples are then centrifuged at 4000 RPM.

The plasma is harvested and the content of IFN-gamma is determined by ELISA, ELISPOT or by a cytometry related procedure LUMINEX assay, Luminex, Austin, Tex., USA).

As an alternative, one can use wild JC virus that can be obtained from cerebrospinal fluid of PML patients and cultured on human embryonic glial cells.

To detect production of IFN-gamma, it is also possible to destroy the red cells and mark the cells with anti-CD3/CD4/CD8 antibodies. IFN-gamma is then detected with the cells after they are permeabilized. It is also possible to plate activated PBMC on anti-IFN-γ coated plates then to numerate IFN-γ producing cells following an ELISPOT procedure.

Useful references comprise Major et al., (J Virol 1987, 61:1435-1441), Frye et al., (J Virol Methods 1997, 63:81-92), Gasnault et al., (AIDS. 2003 Jul. 4; 17(10):1443-9.).

The invention claimed is:

1. A method of detecting activated effector helper T lymphocytes against JC virus in a patient, the method comprising:
    exposing a blood sample from said patient to epitopes of JC virus for a period of time of less than 48 hours; and
    detecting the presence, in said blood sample, of T lymphocytes re-stimulated in vitro by exposure to said epitopes, which T-lymphocytes are effector helper T lymphocytes that have previously been activated in vivo by JC virus, wherein
    said detecting is performed by detection of at least one inflammatory cytokine secreted by said T lymphocytes upon presentation of said epitopes of JC virus to said T lymphocytes, said blood sample is taken from a patient who already receives or is set to receive an immunosuppressive treatment.

2. The method of claim 1, wherein said blood sample is exposed to said epitopes by exposing the blood sample to purified JC virus.

3. The method of claim 1, wherein said cytokine is selected from the group consisting of gamma-interferon and interleukin 2.

4. The method of claim 1, wherein said cytokine is detected by ELISA, ELISPOT or flow cytometry.

5. The method of claim 1, wherein said blood sample is a whole blood sample.

6. The method of claim 1, wherein said blood sample is exposed to said epitopes of JC virus for a period of time of less than 24 hours.

7. The method of claim 1, wherein said blood sample is exposed to said epitopes of JC virus for a period of time between 14 and 24 hours.

8. The method of claim 1, further comprising the step of: screening or quantifying for the presence of JC virus in a cerebrospinal fluid sample from said patient.

9. The method of claim 8, wherein said screening or quantifying is performed by PCR or quantitative PCR assay.

10. The method of claim 1, wherein said immunosuppressive treatment is treatment with natalizumab or efalizumab.

11. The method of claim 1, wherein said patient has not yet received immunosuppressive treatment.

12. The method of claim 1, wherein said patient is already receiving an immunosuppressive treatment.

13. The method of claim 12, further comprising monitoring the immunosuppressive treatment of the patient, wherein said immunosuppressive treatment is continued if no activated T-lymphocytes against JC virus are detected in the blood sample of the patient.

14. The method of claim 1, wherein said patient presents a sign or symptom of Progressive Multi-focal Leukoencephalopathy.

* * * * *